(12) United States Patent
Shipp et al.

(10) Patent No.: US 9,155,550 B2
(45) Date of Patent: Oct. 13, 2015

(54) TROCAR CANNULA ANCHOR AND SEAL

(71) Applicant: APOLLO CAMERA, L.L.C., Estill Springs, TN (US)

(72) Inventors: John I. Shipp, Atlantic Beach, FL (US); Jeffrey White, Birchrunville, PA (US)

(73) Assignee: APOLLO CAMERA, L.L.C., Estill Springs, TN (US)

( * ) Notice: Subject to any disclaimer, the term of this patent is extended or adjusted under 35 U.S.C. 154(b) by 0 days.

(21) Appl. No.: 14/195,395

(22) Filed: Mar. 3, 2014

(65) Prior Publication Data

US 2014/0180015 A1    Jun. 26, 2014

Related U.S. Application Data

(60) Continuation of application No. 13/913,120, filed on Jun. 7, 2013, now abandoned, which is a continuation of application No. 12/802,032, filed on May 28, 2010, now Pat. No. 8,466,659, which is a continuation of application No. 11/430,431, filed on May 9, 2006, now abandoned, which is a division of application No. 10/680,973, filed on Oct. 7, 2003, now Pat. No. 7,041,055.

(60) Provisional application No. 60/416,665, filed on Oct. 7, 2002, provisional application No. 60/424,752, filed on Nov. 8, 2002, provisional application No. 60/424,754, filed on Nov. 8, 2002, provisional application No. 60/424,755, filed on Nov. 8, 2002, provisional application No. 60/425,506, filed on Nov. 12, 2002, provisional application No. 60/425,522, filed on Nov. 12, 2002, provisional application No. 60/425,523, filed on Nov. 12, 2002, provisional application No. 60/439,759, filed on Jan. 13, 2003.

(51) Int. Cl.
| | |
|---|---|
| *A61B 1/32* | (2006.01) |
| *A61B 17/22* | (2006.01) |
| *A61B 17/34* | (2006.01) |
| *A61B 17/221* | (2006.01) |
| *A61B 17/02* | (2006.01) |

(52) U.S. Cl.
CPC ....... *A61B 17/22031* (2013.01); *A61B 17/0218* (2013.01); *A61B 17/221* (2013.01); *A61B 17/34* (2013.01); *A61B 17/3421* (2013.01); *A61B 17/3423* (2013.01); *A61B 17/3439* (2013.01)

(58) Field of Classification Search
USPC ............... 600/201–219; 604/164.01–164.04, 604/164.1, 164.11, 164.07
See application file for complete search history.

(56) References Cited

U.S. PATENT DOCUMENTS 3,817,251 A * 6/1974 Hasson ........................ 604/26
4,608,965 A * 9/1986 Anspach et al. ............. 600/101
(Continued)

*Primary Examiner* — Matthew J Kasztejna
(74) *Attorney, Agent, or Firm* — Martin & Ferraro, LLP

(57) ABSTRACT

A cannula assembly for use in laproscopic surgery includes a cannula having a proximal end for use in orientating the assembly into an abdominal cavity, a distal end for insertion into a patient, and a passage through which surgical instruments can be inserted. An expandable feature in the form of an anchor is located toward the distal end of the cannula and is selectively expandable and collapsible. The feature in its expanded state prevents withdrawal of the cannula. A collar is pushed distally until it releasably cinches to the outside of the abdominal cavity thereby creating an airtight seal and stabilizing the assembly. The collar has a friction fit with the cannula designed to prevent excessive force against the cavity walls.

9 Claims, 2 Drawing Sheets

(56) References Cited

U.S. PATENT DOCUMENTS

| | | |
|---|---|---|
| 5,002,557 A | 3/1991 | Hasson |
| 5,147,316 A * | 9/1992 | Castillenti ............... 604/164.04 |
| 5,217,441 A | 6/1993 | Shichman |
| 5,330,497 A | 7/1994 | Freitas et al. |
| 5,697,946 A | 12/1997 | Hopper et al. |
| 6,451,041 B1 * | 9/2002 | Moenning et al. ............ 606/185 |
| 6,451,042 B1 * | 9/2002 | Bonutti ......................... 606/190 |
| 8,435,174 B2 * | 5/2013 | Cropper et al. ............... 600/203 |

\* cited by examiner

TROCAR CANNULA ANCHOR AND SEAL

RELATED APPLICATIONS

This application is a continuation of U.S. application Ser. No. 13/913,120, filed Jun. 7, 2013; which is a continuation of U.S. application Ser. No. 12/802,032, filed May 28, 2010 (now U.S. Pat. No. 8,466,659); which is a continuation of U.S. application Ser. No. 11/430,431, filed May 9, 2006 (now abandoned); which is a divisional of U.S. application Ser. No. 10/680,973, filed Oct. 7, 2003 (now U.S. Pat. No. 7,041,055); which claims the benefit of U.S. Provisional Application No. 60/416,665, filed Oct. 7, 2002; U.S. Provisional Application Nos. 60/424,752; 60/424,754; and 60/424,755, each filed Nov. 8, 2002; U.S. provisional Application Nos. 60/425,506; 60/425,522; and 60/425,523, each filed Nov. 12, 2002; and U.S. Provisional Application No. 60/439,759, filed Jan. 13, 2003; all of which are incorporated by reference herein.

BACKGROUND OF THE INVENTION

1. Field of the Invention

This invention relates to a stabilized cannula adapted to seal against the loss of gas pressure from a body cavity of a patient during a surgical procedure.

2. Description of the Prior Art

The insertion of a cannula into an abdominal cavity during laparoscopic surgery is generally accomplished using one of two methods. In the first method, a hollow needle is inserted into the body cavity prior to the insertion of the cannula so that the cavity can be expanded with a gas, such as carbon dioxide. Thereafter, the cannula is inserted along with a removable sharp obtruator. The obtruator blade cuts through the abdominal wall allowing the surrounding cannula to penetrate into the interior of the cavity. The obtruator is then removed leaving an entry port for various laparoscopic tools to be inserted into the cavity. The cannula is equipped with a seal at its proximal end to ensure that the cavity remains pressurized with the insertion and removal of various instruments. Pressure loss between the cannula and the cavity wall is reduced by the tightness of the fit between the cannula and the cavity wall because the outside diameter of the cannula is larger than the obtruator entry wound. Generally, the obtruator used in this method is equipped with a spring-activated shield that is designed to cover the blade as soon as the interior wall is penetrated to avoid inadvertent puncturing of the organs present inside the cavity. These shields sometimes fail to close quickly enough to avoid injuries, particularly if an organ such as the bowel is attached to the cavity wall.

A known method that avoids injuries associated with the obtruator shield involves direct incision of the wall by the surgeon. Using a small scalpel, the surgeon makes an incision through the cavity wall into the abdominal cavity and inserts a finger into the cavity to feel for organs that might be attached to, or near the abdominal wall. Upon a determination that no organs are attached to the abdominal wall, a cannula with an obtruator having a blunt tip is inserted through the cut. After placement of the cannula, the obtruator is removed. The purpose of the blunt tip of the obtruator is to guide the cannula through the cut down to wound.

Both of the above described methods of insertion are prone to gas leakage and the lack of a proximal-to-distal stability of the cannula. Various techniques have been attempted to minimize these problems. Known anchors for use with laparoscopic cannula have employed threaded sleeves adapted to be secured to the cannula and screwed into a laparoscopic puncture opening to secure the instrument in place. An anchor of this type is found in U.S. Pat. No. 5,217,441. U.S. Pat. No. 5,002,557 to Hasson discloses an inflatable balloon that seals the cannula against the inside wall of the cavity and stabilizes the cannula by employing a tapered collar that cinches against the outside wall of the cavity, in effect sandwiching the cavity wall between the collar and the inflated balloon. The Hasson device provides a sufficient seal and adequate cannula stability, but is difficult to operate. The balloon must be inflated with an external hypodermic syringe or other means through a stop cock. Additionally, sealing the cannula with the cavity wall involves three steps: inflating the balloon, pushing a tapered collar snugly against the external surface of the cavity wall, and securing the collar in place with a set screw. U.S. Pat. No. 5,697,946 to Hopper et al. discloses a balloon-anchoring device that does not require the use of a proximal collar, but instead relies on a portion of the inflating surface to come in contact with the entry wound, thereby wedging the cannula into position. The Hopper device also involves an external inflation device such as a hypodermic syringe connected to the cannula by a stop cock or check valve.

U.S. Pat. No. 5,330,497 to Freitas et al. describes an anchored cannula that uses an expandable mushroom-shaped anchor that in one embodiment opens when the user turns a detented actuator. The anchor cinches-up against the peritoneum when a seal is forced distally. The Freitas device offers an improvement over threads, but still suffers from several drawbacks. In particular, the Freitas device is unduly complex at least in that it requires multiple steps in order to expand the anchor and seal the external cavity wall. A multiplicity of steps during a surgical procedure can lead to a serious inefficiency. Devices that are simple to operate make the procedure more efficient and lead to less errors. Therefore what is needed is a simple, easy-to-use cannula anchoring and sealing device and method for use in laparoscopic surgery.

SUMMARY OF THE INVENTION

In accordance with the purposes of the present invention, as embodied and broadly described herein, a cannula assembly of this invention is provided for permitting the insertion of instruments into a body cavity. The cannula assembly includes a proximal end, a distal end, and a longitudinal axis, an inner sleeve, an outer sleeve coaxial with the inner sleeve, and a collar. The outer sleeve is fixedly attached to the inner sleeve at the distal end of the cannula and has an exterior surface. The outer sleeve forms an anchor that is radially expandable from the longitudinal axis from a retracted position to an expanded position to anchor the cannula assembly to the body of a patient. The collar has an internal surface adapted to form a friction fit with the exterior surface of the outer sleeve to permit the collar to move a portion of the outer sleeve relative to the inner sleeve and move the anchor from the retracted position to the expanded position when the collar is moved toward the distal end of the cannula assembly. The friction fit between the collar and the outer sleeve is configured to permit the collar to move relative to the outer sleeve only toward the distal end of the cannula assembly when the anchor is in the expanded position.

In accordance with the purposes of another embodiment of the present invention, as embodied and broadly described herein, a method of this invention is provided for anchoring and sealing a cannula assembly to the body of a patient. The method includes providing the cannula assembly having a proximal end, a distal end, a radially expandable anchor proximate the distal end, and a longitudinally movable collar; inserting the cannula assembly to a depth sufficient to place the anchor in a retracted position within the patient; and expanding the anchor by moving the collar toward the distal end of the cannula assembly.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

DETAILED DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

Figure 1:
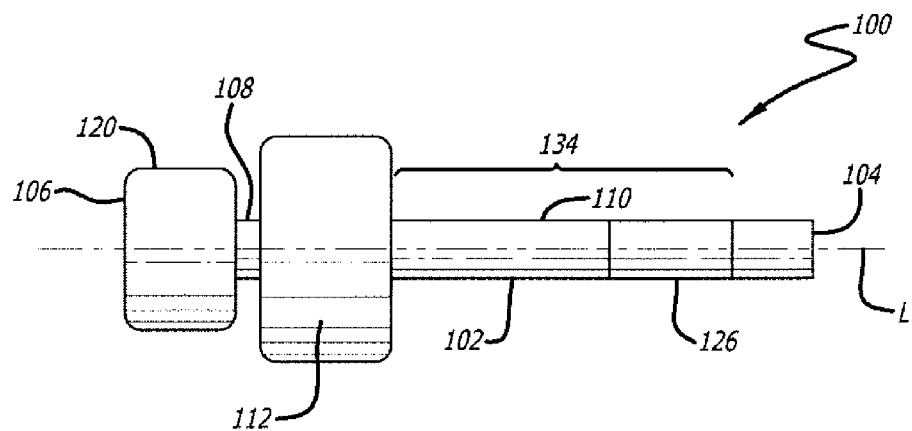
FIG. 1 is a side elevation view of a cannula assembly according to one preferred embodiment of the present invention having an anchor in a retracted position.

FIGS. 1-4 show a trocar cannula assembly for use with the present invention generally referred to by the number 100. As shown in FIG. 1, cannula assembly 100 includes a cannula 102 having a distal end 104, a proximal end 106 opposite distal end 104 along a longitudinal axis L, an inner sleeve 108, and an outer sleeve 110 that is preferably coaxial with inner sleeve 108; and a movable annular collar 112.

Figure 3:
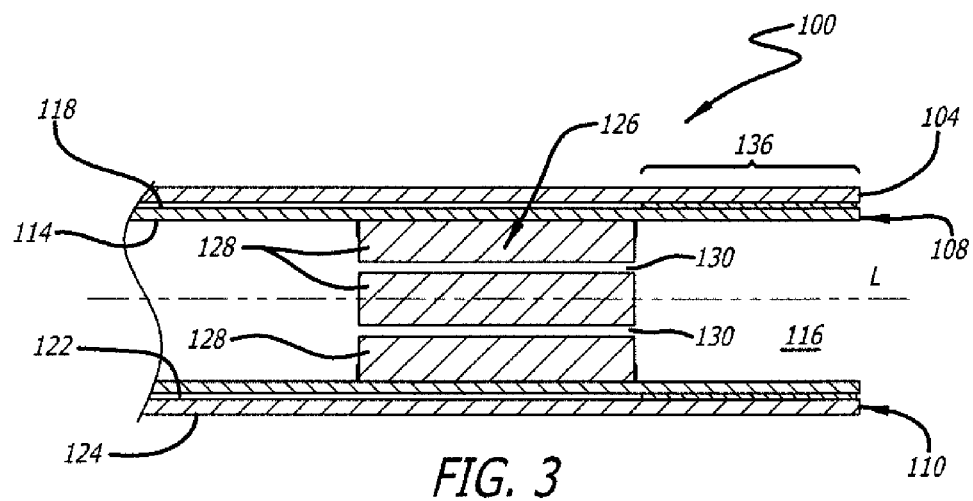
FIG. 3 is a fragmentary cross-sectional side view of the cannula assembly of FIG. 1 with the anchor shown in the retracted position.

As shown in FIG. 3, inner sleeve 108 has an interior surface 114 forming a passage 116 through which one or more instruments may pass, and an exterior surface 118. Referring again to FIG. 1, inner sleeve 108 has a proximal portion 120 that preferably includes a valve and/or seal to maintain pressure when the cannula is inserted into a pressurized cavity.

As shown in FIGS. 1 and 3, outer sleeve 110 has an interior surface 122 and an exterior surface 124. At least a portion of interior surface 122 is preferably adapted for slidable engagement with exterior surface 118 of inner sleeve 108. Outer sleeve 110 forms an anchor 126 preferably located toward distal end 104 of cannula 102. Anchor 126 provides stability to the cannula assembly when deployed within the abdominal cavity, as will be described in more detail below.

FIG. 3 shows anchor 126 preferably having a plurality of finger hinges 128 that are each separated by a slit 130. When anchor 126 moves from a retracted position shown in FIG. 3 to an expanded position shown in FIG. 4, fingers 128 radially expand away from longitudinal axis L of cannula 102 to anchor the cannula assembly to the patient. In order to prevent internal tissue from becoming entangled within fingers 128, anchor 126 preferably includes a flexible cover membrane 132. Cover 132 may be resilient to bias anchor 126 to the retracted position to permit easy insertion of cannula 102 into the abdominal cavity.

Inner sleeve 108 and outer sleeve 110 are preferably joined at distal end 104 of cannula 102 by conventional bonding materials. It will be appreciated by those skilled in the art that other ways to join the inner and outer sleeves together, whether chemically (e.g., glue), physically (e.g., ultrasonically weld or heat application), or mechanically, may be used and are within the broad scope of the present invention.

FIG. 1 shows an annular collar 112 preferably surrounding at least a portion of exterior surface 124 of outer sleeve 110. Annular collar 112 preferably has an internal surface that forms a friction fit with exterior surface 124 to sealingly engage the outer surface of the body cavity when anchor 126 is inserted into the patient and deployed. Preferably, annular collar 112, outer sleeve 110, and inner sleeve 108 are constructed such that the force of the friction fit between annular collar 112 and outer sleeve 110 is greater than the friction force acting between outer sleeve 110 and inner sleeve 108. This may be accomplished, for example, by selecting a material and snugness of fit between annular collar 112 and exterior surface 124 of outer sleeve 110 and the fit between internal sleeve 108 and outer sleeve 110. This permits inner sleeve 108 to move relative to outer sleeve 110 before annular collar 112 will move relative to outer sleeve 110. The interaction between inner sleeve 108, outer sleeve 110, and annular collar 112 is described in more detail below. It will be appreciated that annular collar 112 may exist in a variety of shapes and sizes, and need not completely surround outer sleeve 110 in order to function for its intended purpose.

Having described the physical components of one preferred embodiment of the present invention, a method for its operation will now be described. Returning now to FIG. 1, cannula assembly 100 is positioned proximate the surgical site to be operated upon, such as the abdominal cavity, with annular collar 112 in its proximal-most position and anchor 126 in the retracted position. An obtruator is placed through proximal portion 120, into passage 116 of inner sleeve 108, and beyond distal end 104 of cannula 102.

The distal-most end of the obtruator is generally blade-shaped and punctures the abdominal cavity, allowing cannula 102 to be forced into the defect. Cannula 102 is inserted into the puncture to a sufficient depth so that anchor 126 is below the peritoneum of the abdominal cavity. The obtruator is then removed from cannula 102.

With cannula assembly 100 properly positioned and inserted into the abdominal cavity, anchor 126 is deployed. Holding proximal portion 120 stationary, annular collar 112 is moved away from proximal portion 120 toward distal end 104. Annular collar 112 is preferably tightly fitted around external surface 124 of outer sleeve 110 to form a friction fit such that movement of annular collar 112 will cause a corresponding movement of a movable portion 134 of outer sleeve 110, which includes anchor 126. As annular collar 112 moves in the distal direction, movable portion 134 of outer sleeve 110 runs against a stationary portion 136 of outer sleeve 110, which is joined to inner sleeve 108 at distal end 104. Finger hinges 128 of anchor 126 radially expand away from longitudinal axis L to deploy anchor 126 into an arc shape so that anchor 126 moves from the retracted position shown in FIG.

Figure 4:
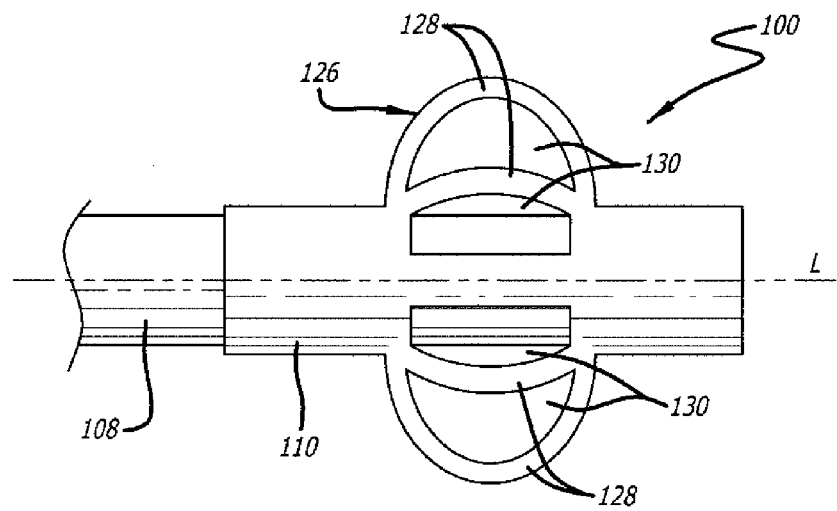
FIG. 4 is a fragmentary side elevation view of the cannula assembly of FIG. 1 with the anchor shown in the expanded position.

3 to the expanded position shown in FIG. 4. As annular collar 112 and outer sleeve 110 continue to move distally, anchor 126 becomes fully deployed.

Figure 2:
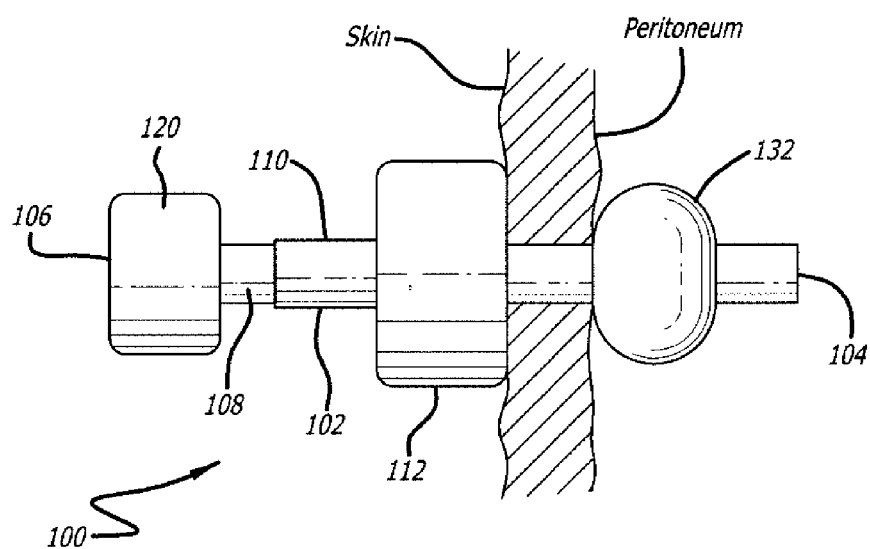
FIG. 2 is a side elevation view of the cannula assembly of FIG. 1 with the anchor deployed in the abdominal cavity in an expanded position and a collar distally applied against the exterior of the abdominal cavity.

Once anchor 126 becomes fully deployed, movable portion 134 of outer sleeve 110 reaches its maximum longitudinal distance of travel and becomes stationary. At this point, the force of the friction fit between annular collar 112 and outer sleeve 110 is overcome by the force being applied to move annular collar 112 toward distal end 104. Annular collar 112 begins to move relative to outer sleeve 110 and cinches-up against the outer surface of the abdominal wall as shown in FIG. 2. After annular collar 112 is sufficiently pressed against the skin so that both sides of the abdominal cavity are sealed between annular collar 112 and anchor 126, annular collar 112 and proximal portion 120 are released.

While released, annular collar 112 and anchor 126 maintain a compression of the abdominal wall between them. Movement of annular collar away from the abdominal wall is retarded by the friction fit between annular collar 112 and outer sleeve 110. Anchor 126, owing to the resiliency of membrane 132 and to the elasticity of fingers 128, supplies a force that tends to restore the position of outer sleeve 110 relative to inner sleeve 108 to its original position. The surfaces and/or materials of outer sleeve 110 and inner sleeve 108 are designed such that the friction force between them counters the restoring force of anchor 126. Thus, after annular collar 112 is moved distally and anchor 126 is deployed, the friction force between inner sleeve 108 and outer sleeve 110 is larger than the restoring force being exerted from anchor 126 such that the relative position of inner sleeve 108 and outer sleeve 110 is maintained once cannula assembly 100 is released. A sufficient seal between anchor 126 and annular collar 112 is maintained in part because the force of the friction fit between annular collar 112 and outer sleeve 110 is greater than the friction force acting between inner sleeve 108 and outer sleeve 110, which in turn acts to overcome the force biasing anchor 126 to the retracted position.

After the surgical procedure, cannula assembly 100 is removed from the abdominal cavity by moving annular collar 112 toward proximal end 106 of cannula 102. Because the friction force of the friction fit between annular collar 112 and outer sleeve 110 is greater than the friction force between outer sleeve 110 and inner sleeve 108, outer sleeve 110 and inner sleeve 108 move relative to each other with a proximal movement of annular collar 112. Anchor 126 collapses to the retracted position as shown in FIG. 3, thus permitting the withdrawal of cannula assembly 100 from the patient.

To summarize, the user holds proximal portion 120 in one hand and annular collar 112 in the other hand and applies a force separating the two. This action moves portion 134 of outer sleeve 110 and inner sleeve 108 relative to one another, and therefore deploys anchor 126. As annular collar 112 and the movable portion of outer sleeve 110 continue to move toward distal end 104, anchor 126 becomes fully deployed. Thereafter, annular collar 112 begins to move relative to outer sleeve 110 and cinches-up against the skin. The friction fit force between annular collar 112 and outer sleeve 110 is preferably sized such that the force needed to overcome the friction fit force to move annular collar 112 relative to outer sleeve 110 is within the safe limits to prevent over insertion of cannula assembly 100 into the abdominal cavity.

Cannula assembly 100 may be used in surgeries other than laproscopic surgery. Additionally, it will be appreciated that other forms of anchors may be used with the cannula of the present invention and still remain within the broad scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A cannula assembly for surgery on tissue at a surgical site in a body of a patient, the cannula assembly having a proximal end, a distal end, and a longitudinal axis, said cannula assembly comprising:
    an inner sleeve;
    an outer sleeve coaxial with said inner sleeve, said outer sleeve being fixedly attached to said inner sleeve at the distal end, said outer sleeve including a movable portion defined intermediate the proximal end and the distal end, a stationary portion defined proximate the distal end, an exterior surface, and an anchor defined on said exterior surface, said anchor, upon movement of said movable portion toward the distal end into contact with said stationary portion, being radially expandable from a retracted position along the longitudinal axis to an expanded position to anchor said cannula assembly to the body of a patient; and
    a collar having an internal surface adapted to form a friction fit with said exterior surface of said outer sleeve to permit said collar to move the movable portion of said outer sleeve relative to said inner sleeve toward the distal end and move said anchor from the retracted position to the expanded position when said collar is moved toward the distal end, the friction fit being configured, after said anchor is expanded to the expanded position, to prevent said collar from moving relative to said outer sleeve toward the proximal end.

2. The cannula of claim 1, wherein said anchor includes a plurality of finger hinges, said collar being adapted to move said movable portion of said outer sleeve to move said finger hinges from the retracted position to the expanded position.

3. The cannula assembly of claim 2, wherein said finger hinges are separated from one another by slits.

4. The cannula assembly of claim 2, wherein said anchor includes a membrane covering said finger hinges to prevent entanglement of the tissue with said finger hinges.

5. The cannula assembly of claim 1, wherein said anchor is configured for insertion in the retracted position into an abdominal cavity of the body of the patient, and wherein said anchor, when expanded from the retracted position to the expanded position inside the abdominal cavity of the patient, anchors said cannula assembly to the body of the patient.

6. The cannula assembly of claim 5, wherein a portion of an abdominal wall of the patient is compressed between said anchor and said collar to anchor said cannula assembly to the body of the patient.

7. The cannula assembly of claim 6, wherein compression between said anchor and said collar against the portion of the abdominal wall of the patient defines a seal on the portion of the abdominal wall of the patient.

8. The cannula assembly of claim 5, wherein said inner sleeve includes a cavity extending from the proximal end to the distal end of the cannula assembly, said cavity, when said cannula assembly is anchored to the body of the patent, affording access to the abdominal cavity therethrough.

9. The cannula assembly of claim 5, wherein said inner sleeve includes a proximal end and an enlarged proximal portion proximate said proximal end, said enlarged proximal portion configured to be held by a user during movement of said collar away from said enlarged proximal portion.

* * * * *

UNITED STATES PATENT AND TRADEMARK OFFICE
CERTIFICATE OF CORRECTION

| | | |
|---|---|---|
| PATENT NO. | : 9,155,550 B2 | Page 1 of 1 |
| APPLICATION NO. | : 14/195395 | |
| DATED | : October 13, 2015 | |
| INVENTOR(S) | : John I. Shipp et al. | |

It is certified that error appears in the above-identified patent and that said Letters Patent is hereby corrected as shown below:

<u>In the Claims</u>
<u>Column 6, Claim 8</u>:
Line 61: change "patent," to -- patient, --.

Signed and Sealed this
Eighth Day of March, 2016

Michelle K. Lee
*Director of the United States Patent and Trademark Office*